(12) United States Patent
Lacey et al.

(10) Patent No.: US 6,571,611 B2
(45) Date of Patent: Jun. 3, 2003

(54) HIGH TEMPERATURE DIESEL FUEL TEST APPARATUS AND METHOD

(75) Inventors: Paul Lacey, The Woodlands, TX (US); Jose De La Cruz, San Antonio, TX (US); Eliazar H. Saucedo, San Antonio, TX (US); Jack R. Compton, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/067,071

(22) Filed: Feb. 4, 2002

(65) Prior Publication Data

US 2002/0083759 A1 Jul. 4, 2002

Related U.S. Application Data

(63) Continuation-in-part of application No. 09/563,170, filed on May 2, 2000, now Pat. No. 6,370,946.

(51) Int. Cl.[7] ......................... G07N 33/00; G07N 15/06; G07N 25/00
(52) U.S. Cl. ..................... 73/61.62; 73/61.72; 73/61.76
(58) Field of Search ............................ 73/61.62, 61.71, 73/61.72, 61.76, 61.77

(56) References Cited

U.S. PATENT DOCUMENTS

| | | | | |
|---|---|---|---|---|
| 2,039,122 A | * | 4/1936 | Smith ........................ | 73/61.76 |
| 3,059,467 A | * | 10/1962 | Meguerian et al. ........ | 73/61.62 |
| 3,400,575 A | * | 9/1968 | Madden .................... | 73/61.72 |
| 3,505,857 A | * | 4/1970 | Jenkins ...................... | 73/61.72 |
| 5,252,528 A | * | 10/1993 | Voecks et al. .............. | 502/74 |
| 5,299,449 A | * | 4/1994 | Hardy et al. ............... | 73/61.62 |
| 5,492,005 A | * | 2/1996 | Homan et al. ............. | 73/61.62 |
| 5,693,874 A | * | 12/1997 | De La Cruz et al. ...... | 73/61.62 |
| 6,370,946 B1 | * | 4/2002 | Lacey et al. ............... | 73/61.62 |

* cited by examiner

Primary Examiner—Robert Raevis
Assistant Examiner—Michael Cygan
(74) Attorney, Agent, or Firm—Gunn, Lee & Hanor; Michelle Evans

(57) ABSTRACT

Tortuous passageways are provided in a substrate component that is retained within a holding chamber. Fuels and fuel mixtures to be comparatively tested are introduced into the holding chamber and into the tortuous passageways of the substrate component. The substrate component is controllably maintained at an elevated temperature during a specified number of defined test cycles. The substrate component is then removed and its after-test weight compared with an initial weight before the test. The tortuous passageways of the substrate component provide increased surface area subject to deposit formation and extended residence time for fuel to remain in contact with the substrate surface, thereby greatly enhancing the measured difference between tested fuels and fuel mixtures.

19 Claims, 5 Drawing Sheets

HIGH TEMPERATURE DIESEL FUEL TEST APPARATUS AND METHOD

CROSS-REFERENCE TO RELATED APPLICATION

This is a continuation-in-part of application Ser. No. 09/563,170 filed May 2, 2000, now U.S. Pat. No. 6,370,946B1.

BACKGROUND OF THE INVENTION

1. Field of the Invention

This invention relates generally to an apparatus and method for testing various diesel fuels and diesel fuel additives, and more particularly to an apparatus and method for quantitatively predicting the deposition characteristics of various diesel fuels and diesel fuel additives formed during operation of a diesel engine.

2. Description of Related Art

Heretofore it has been extremely difficult to provide test apparatus and methods that consistently provide reliable quantitative evaluations of the deposition and/or cleaning characteristics of various diesel fuels and diesel fuel additives. More importantly, it has been difficult to provide bench test results that correlate with the deposit characteristics experienced during actual engine operation. Often, because of the small surface area of a test component and the resultant short residence time that the test fuel is in contact with the component surface, in addition to environmental and control variables during testing, it has been very difficult to obtain consistent results in repeated bench tests.

For example, the test apparatus described in U.S. Pat. No. 5,693,874 issued Dec. 2, 1997 to Jose L. DeLaCruz, et al. for Test Apparatus and Method for Determining Deposit Formation Characteristics for Fuels, and assigned to the Assignee of the present invention, places a test piece having the shape characteristic of an engine valve in a test chamber. The exposed surface available for deposit formation comprises only a portion of the flanged head of the representative engine valve. As a result of the minimal surface area, i.e., the backswept portion of the valve head, the fuel to be tested is in contact with a relatively small deposition surface for only a very short time. Because of these inherent limitations, it has been necessary to run fuel deposition tests for extended periods of time in order to obtain sufficient weighable deposits, thus contributing to variances in deposition characteristics from test to test. In addition, the necessarily prolonged test periods lessen the sought-after advantage of relatively easy, relatively inexpensive tests to evaluate the deposition characteristics of different fuels and fuel additives.

Several attempts have been made to provide a diesel fuel test apparatus that will accurately and repeatedly produce accurate indications of the tendency for different fuels and fuel additives to form, or remove, deposits on or from fuel delivery and combustion chamber components of an internal combustion engine. In addition to the prior attempts discussed in the Background of the Invention section of the parent application, other test schemes propose distilling the fuel to reduce it in such a manner that the residual fuel includes only the higher viscosity fractions. The residual fuel is passed over a heated inclined ramp, and the flow distance along the ramp and the residual weight of the fuel measured. For example, see U.S. Pat. No. 3,108,468 granted Oct. 29, 1963 to B. L. Mickel for an Engine Fuel Test Device, and U.S. Pat. No. 5,036,699 granted Aug. 6, 1991 to Rolf Fikentscher, et al. for an Apparatus for Testing Fuel Additives and Oil Additives. In the devices described in those patents, and in the prior art in general, there are no teachings directed to the application of a test fuel composition and hot air to a heated substrate having an adequate surface area, distributed over a sufficient length, to enable one to quickly, accurately, and repeatedly assess the deposit removal characteristics of selected fuels and fuel additives.

Furthermore, test apparatus in current use require elastomeric seals to seal the test chamber and the fuel, air and other connections to the test chamber. Elastomeric seals deteriorate rapidly in the presence of heat, fuel and fuel additives, all of which are routinely encountered in diesel fuel testing. As a result of rapid deterioration, elastomeric seals have a very limited service life in hot fuel test environments and must be replaced at relatively short intervals.

The present invention is directed to overcoming the problems set forth above. It is desirable to have a test apparatus that provides a substrate surface that has a surface area and flow length sufficient to provide adequate residence time for the tested fuel mixture to remain in contact with the substrate, and thereby quantitatively demonstrate the deposit forming or cleaning characteristics of the fuel mixture. It is also desirable to have a fuel test apparatus that does not rely on elastomeric seals to provide airtight seals between the various components of the test apparatus.

BRIEF SUMMARY OF THE INVENTION

In accordance with one aspect of the present invention, a diesel fuel test apparatus has a substrate component disposed in a holding chamber. Importantly, the substrate component has a surface at least partially defined by at least one tortuous passageway. The test apparatus further includes a source of fuel selected from the group consisting of diesel fuel, diesel fuel additive substances, and mixtures of diesel fuel and diesel fuel additive substances, the source of fuel being in fluid communication with the holding chamber. Also, the test apparatus includes a source of heated air that is in fluid communication with the holding chamber.

In accordance with another aspect of the present invention, a method for evaluating the deposit forming characteristics of a candidate fuel includes weighing a substrate component having a surface at least partially defined by at least one tortuous passageway, and determining an initial weight of the substrate component. The weighed substrate is then placed in a holding chamber adapted to maintain at least a portion of the substrate component in intimate contact with an interior surface of the holding chamber. Subsequently, a test cycle is carried out that includes introducing a selected quantity of fuel into the holding chamber and onto the defined surface of the substrate component. A stream of air heated to a selected temperature is then passed through the holding chamber for a selected period of time. The introduction of fuel and the passing of heated air through the holding chamber is repeated throughout a number of cycles carried out over a selected period of time, after which the steps of the test cycle are discontinued. The substrate component is again weighed and the weight of the substrate component after discontinuing the test cycle is measured. The difference between the initial weight and the after-test weight of the substrate component is then calculated.

BRIEF DESCRIPTION OF THE SEVERAL VIEWS OF THE DRAWINGS

A more complete understanding of the structure and operation of the present invention may be had by reference to the following detailed description when taken in conjunction with the accompanying drawings, wherein.

DETAILED DESCRIPTION OF THE INVENTION

Heretofore, test apparatus and methods for testing the deposition characteristics of diesel fuels and diesel fuel additives have provided substrate structures, on which the test fuel is deposited, that have only simple planar or curved surfaces available for deposit formation. The primary problem inherent in the prior test devices is insufficient substrate surface and, consequentially, an inadequate fuel residence time for physical contact between the fuel and the deposition surface. Thus, small changes in deposition characteristics have been hard to accurately evaluate, even after prolonged test cycles.

Figure 1:
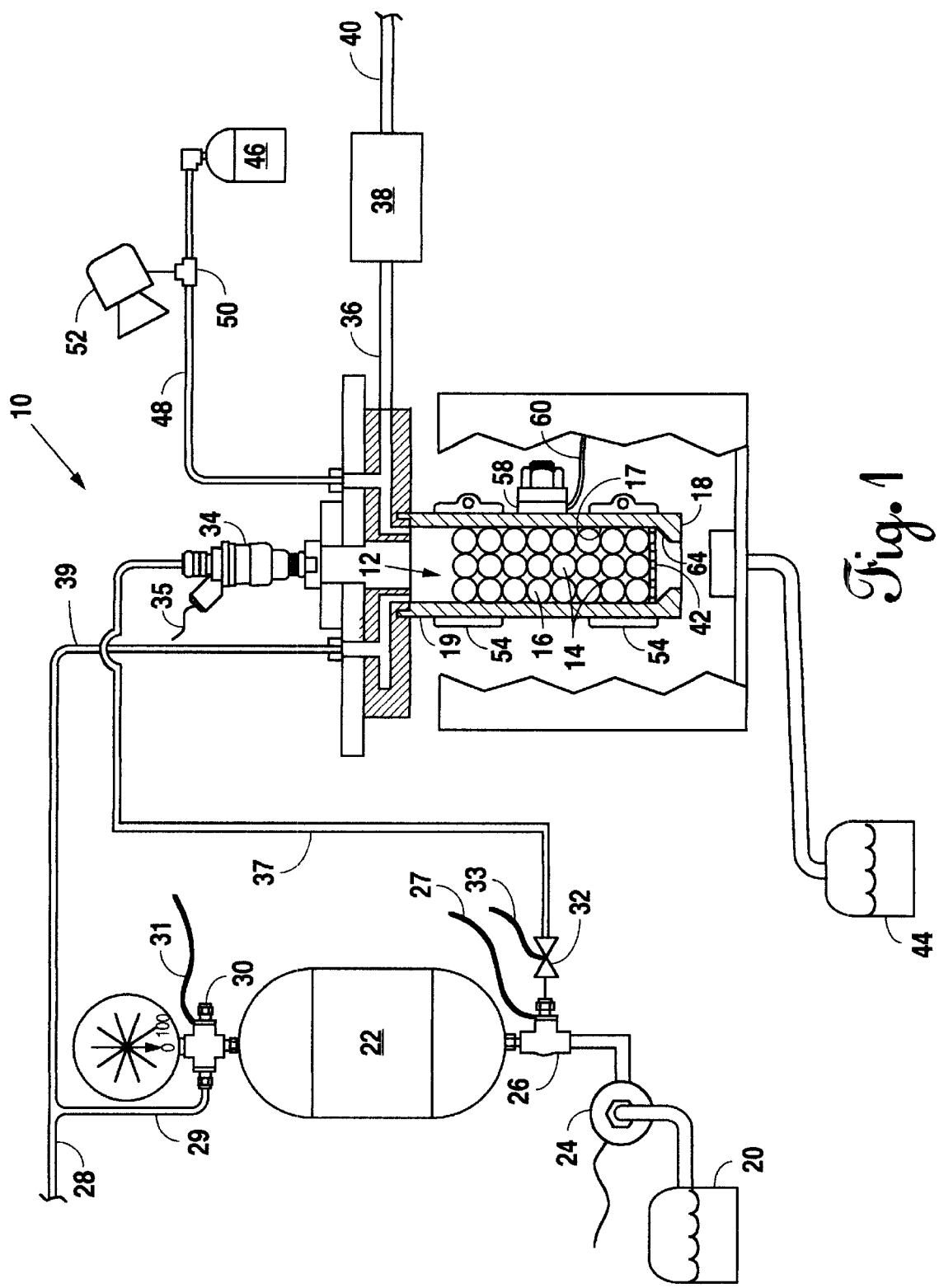
FIG. 1 is a somewhat schematic diagram of a high temperature diesel fuel test apparatus embodying the present invention.

The high temperature diesel fuel test apparatus embodying the present invention is generally indicated in FIG. 1 by the reference numeral 10. The test apparatus 10 includes a substrate component 12 having a fuel deposition surface that is at least partially defined by one or more tortuous passageways 14. The term "tortuous" as used herein means "full of elongated winding or twisting curved passageways." In the preferred embodiment of the present invention, a plurality of tortuous passageways 14 are defined by the exterior surfaces of a plurality of adjacent, abuttingly disposed, spheres 16. In a representative construction of the preferred embodiment, the spheres 16 are grade 25, ¼ inch hardened steel ball bearings. Ball bearings offer several advantages over other substrates in that they are relatively inexpensive, have very consistent surface finish bearing-to-bearing, and therefore contribute to test results that are highly reproducible from test to test. Also, ball bearings have a large surface area to mass ratio, thereby improving the sensitivity of the substrate component to the weight measurement of formed deposits. During testing, a candidate fuel undergoing test, heated air, inert gas, and/or other substances as described below, flow around, between, over and under the adjacently disposed spheres, aided by gravity and the pressure of the fuel, heated air and other substances such as inert gas flowing through a containment chamber.

In the preferred embodiment of the present invention, the containment chamber is a cylindrical holding chamber 18 having an interior surface 17 and an exterior surface 19. The term "holding chamber" as used herein means "a chamber that is adapted to retain possession of, to receive and retain, or to hold something, such as a receptacle."

A source of diesel fuel 20 is provided to the holding chamber 18 by a conduit 37. The term "diesel fuel" as used herein means "diesel fuel, diesel fuel additive substances, such as detergents and other cleaning or scrubbing agents, and mixtures of diesel fuel and diesel fuel additive substances." Diesel fuel is initially conveyed to a fuel reservoir 22, which in the preferred embodiment is a pressurizable tank, by a fuel pump 24. When desired, the fuel pump 24 pumps diesel fuel from the source 20 into the fuel reservoir 22 through a first, or lower, 3-way valve 26. The lower 3-way valve 26 is controlled by a control signal 27. The lower 3-way valve 26 is completely closed at a first position and fuel flow from the pump 24 is blocked, thereby preventing a flow of fuel into the fuel reservoir 22. At a second position of the 3-way valve 26, fuel flow is directed from the pump 24 to the fuel reservoir 22. In yet a third position, the lower 3-way valve 26 directs fuel flow from the fuel reservoir 22 to a 2-way valve 32.

A source of an inert gas 28, such as bottled nitrogen, is conveyed by a conduit 29 to a second, or upper, 3-way valve 30 located at the top of the pressurizable fuel reservoir 22. A control signal 31 controls operation of the upper 3-way valve 30, as follows: At a first position the valve 30 is completely closed, thereby preventing a flow of inert gas into the upper portion of the pressurizable fuel reservoir 22. At a second position, the upper 3-way valve 30 directs a flow of inert gas through the conduit 29 to the upper portion of the fuel reservoir 22. At a third position of the upper 3-way valve 30, the upper portion of the fuel reservoir 22 is opened to atmosphere, thereby reducing any residual gas pressure in the top portion of the fuel reservoir 22.

When it is desired to pump fuel into the fuel reservoir 22, the upper 3-way valve 30 is first moved to the third position at which the upper portion of the fuel reservoir 22 is opened to atmosphere. The lower 3-way valve is then moved to its second position at which fuel is pumped directly into the fuel reservoir 22 until the fuel reservoir 22 is substantially filled with the test fuel. After filling, the upper 3-way valve 26 is moved to the second position at which a flow of inert gas is conducted from the conduit 29 to the upper portion of the fuel reservoir 22, thereby pressurizing the fuel reservoir 22. When a pressurized flow of the test fuel is desired, the lower 3-way valve 26 is moved to its third position at which a flow of fuel, under pressure by the inert gas, is directed to a 2-way fuel valve 32. The 2-way valve 32 serves as a shutoff valve controlled by a control signal 33. When the lower 3-way valve 26 is at its third position, and the 2-way fuel valve 32 is at an open position, a flow of fuel is supplied through a conduit 32 to a fuel injector 34 disposed in a top opening of the holding chamber 18. The operation of the fuel injector 34 is controlled by a control signal 35 which controls the opening, closing, and pulse duration of the fuel injector 34.

A source of heated air 36 is directed through a heat exchanger 38 to the holding chamber 18. A controllable source of pressurized air is conveyed by a conduit 40 to the heat exchanger 38.

Desirably, a means for providing a continuous flow of inert gas through the holding chamber 18, when the chamber is sealed, comprises an open conduit 39 extending from the source of inert gas 28, such as a nitrogen under pressure in a tank or bottle, to the holding chamber 18. A continuous flow of inert gas through the holding chamber 18 during testing advantageously provides an inert gas cover inside the holding chamber that reduces any potential for fire or explosion of an air/fuel mixture in the chamber 18.

A retainer plate 42 is disposed above a convergent conical opening 64 at the bottom of the holding chamber 18. The retainer plate 42 is perforated to permit the free passage of fuel, air, inert gas, or other fluids from the holding chamber 18. Furthermore, in the preferred embodiment, the perforated retainer plate 42 serves to retain the spheres 16 in fixed relationship within the holding chamber 18.

Another desirable component of the apparatus 10 includes a $CO_2$ fire extinguisher 46 connected to the holding chamber 18 by a conduit 48. A flow of $CO_2$ gas to the holding chamber 18 is controlled by a 2-way valve 50 operationally disposed in the conduit 48 at a position between the $CO_2$ extinguisher 46 and the holding chamber 18. Operation of the 2-way valve 50 is controlled by an infrared heat sensor 52 directed at the test area so that it can sense an excessive heat or fire condition.

Figure 2:
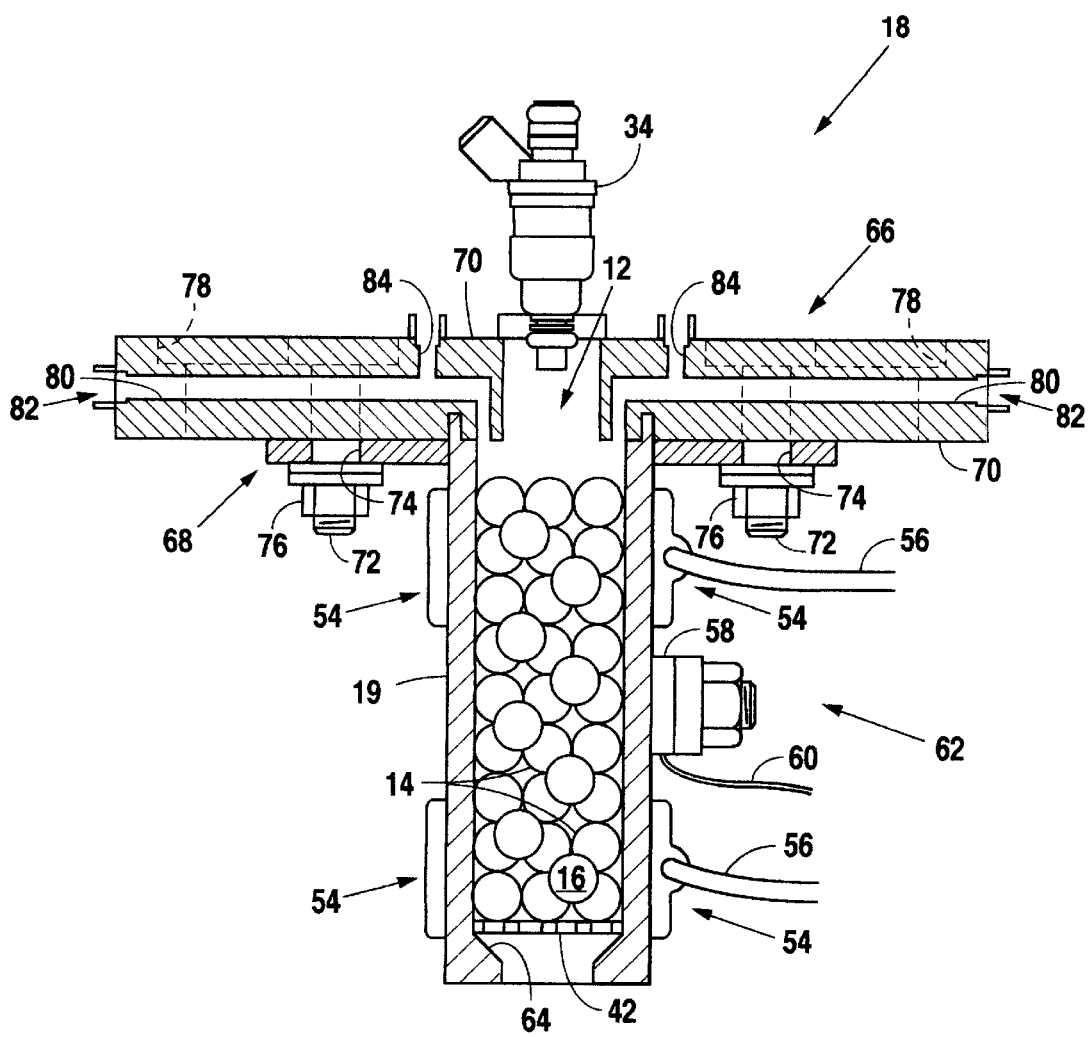
FIG. 2 is an enlarged cross-sectional view of primary portions of the high temperature diesel fuel test apparatus illustrated in FIG. 1, with certain components of the apparatus shown in elevation for clarity.

Turning to FIG. 2, a means for heating the substrate includes two circumferential heaters 54 disposed around the exterior surface 19 of the holding chamber 18. Electric current is controllably supplied to the circumferential heaters 54 by an electrical wire 56. The temperature of the exterior surface 19 of the holding chamber 18 is sensed by a thermocouple 58 that delivers a temperature signal 60 to a conventional control system, such as a programmable controller or computer, which regulates electrical current directed to the heaters 54.

The holding chamber 18 has a first portion 62 that forms a cylindrical body and a second portion 66 that provides a mounting flange for the first portion 62. The second portion 66 includes a first plate 68 that is advantageously attached to the first portion 62 of the holding chamber 18 in fixed metal-to-metal contact, such as by welding, as illustrated in the drawings. The fixed metal-to-metal joint provides a sole means by which an airtight seal is formed between the holding chamber 18 and the first plate 68 of the flange portion 66.

The second, or flange, portion 66 also includes a second plate 70. The first plate 68 and the second plate 70 are secured together by mounting bolts 72 extending through respective holes 74 provided in the second plate 70 and the first plate 68. The heads of the mounting bolts 72 are disposed in elongated adjustment slots 78 provided in the second plate 70 and secured by nuts 76. Importantly, when the first plate 68 and the second plate 70 are joined together in biased contact as provided by the bolts 72 and nuts 76, the second plate 70 is removably attached to the first plate 68 in biased metal-to-metal sufficient to provide a sole means by which an airtight seal is formed between the first plate 68 and the second plate 70 of the mounting flange 66.

A plurality of internally disposed transverse passageways 80 are formed in the second plate 70 and extend between a respective one of peripheral openings 82, provided on the outer perimeter of the second plate 70, to the interior of the holding chamber 18. Vertical passageways 84 extend from the upper surface of the second plate 70 and intersect with a respective one of the internally disposed transverse passageways 80, thereby providing fluid communication through the second plate 70 of the mounting flange 66 and into the interior of the holding chamber 18. Importantly, the heated air conduits 36, the inert gas conduit 39, and the $CO_2$ conduit 48 are connected respectively to the vertical passageways 84 and the transverse passageways 80 in biased metal-to-metal contact sufficient to provide a sole means by which an airtight seal is formed between the metallic conduits 36/39/48 and the top plate 70 of the mounting flange 66. In a similar manner, gases representative of engine exhaust gas or liquid additives may be conveyed by additional metallic conduits and introduced into the holding chamber 18 through the transverse and/or the vertical passageways 80/84. Such additional metallic conduits are also desirably connected to respective openings in the second plate 70 in biased metal-to-metal contact sufficient to provide a sole means by which an airtight seal is formed between the respective additional metallic conduits and the second plate 70.

Figure 3:
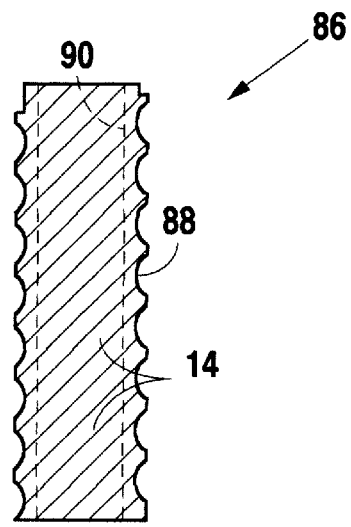
FIG. 3 is an elevational view of a representative alternate substrate member embodying the present invention.
Figure 4:
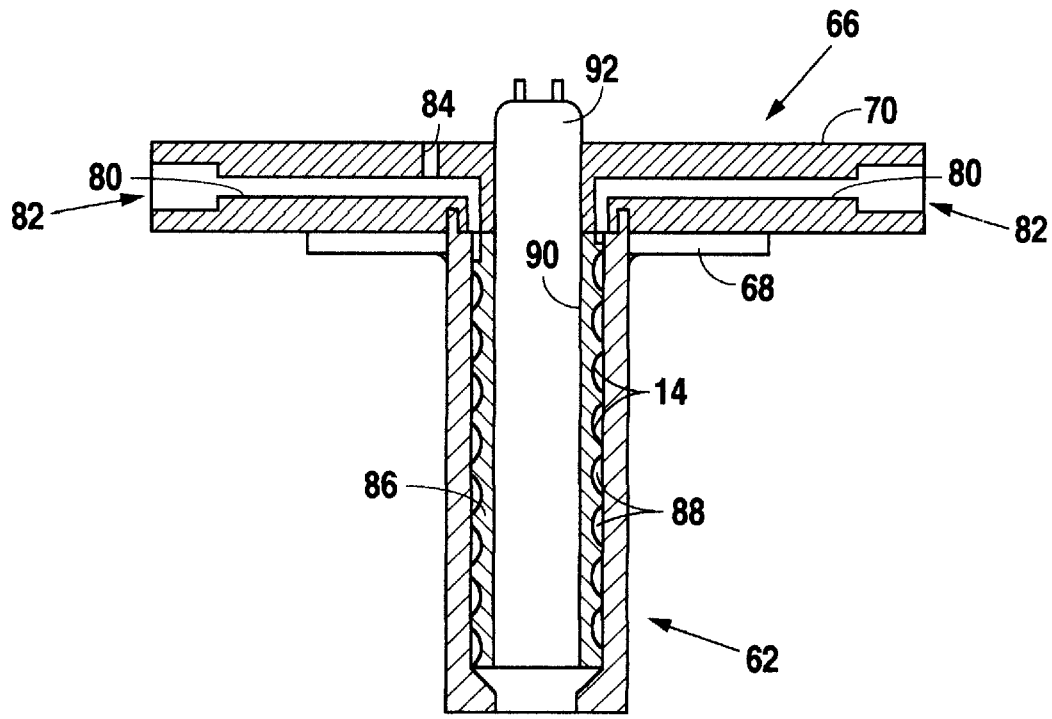
FIG. 4 is a simplified cross-sectional view of primary portions of the test apparatus with the representative alternate substrate member of FIG. 3 enclosed within a holding chamber.

In an alternate embodiment of a substrate component, illustrated in FIGS. 3 and 4, a single one-piece substrate component 86 is disposed within the holding chamber 18. In the alternate substrate component 86, the tortuous passageways 14 are defined by a plurality of curvilinear passageways 88 defined in the exterior surface of the alternate substrate component 86. The term "curvilinear passageway," as used herein, means "any of several curvilinear passageways, such as a helicoid or similar surface having a spiral form, or tortile surfaces defined by twisting or winding curves." Specifically, the curvilinear passageways 88 provide elongated passageways over which fuel and hot air flow during respective cyclic interjections.

Desirably, the alternate substrate component 86 is snugly received within the interior surface 17 of the holding chamber 18. By way of example, in an illustrative construction, the interior bore 17 of the holding chamber 18 has a diameter of 19.61 mm (0.772 in.) The outer diameter of the alternate substrate component 86 has a diameter of 19.56 mm (0.770 in.). This provides a radial clearance of only 0.025 mm (0.001 in.). As a result of the close fit between the alternate substrate component 86 and the interior surface 17 of the holding chamber 18, passage of fuel and air between adjacent curvilinear passageways 88 is inhibited. Thus, the curvilinear passageways 88 are substantially fully defined by the spirals formed on the exterior surface of the substrate component 86 in cooperation with the curved interior bore 17 of the holding chamber 18.

The alternate substrate component 86 has a smooth interior bore 90. An alternate heating means 92, such as a cartridge heater, is snugly disposed within the interior bore 90 and provides a means by which the substrate component 86 is heated to a selected temperature.

In the alternate embodiment, fuel flow to the surface of the substrate component 86 is delivered through one or more of the transverse passageways 80 or in cooperation with one or more vertical passageways 84 that intersect with a respective transverse passageway 80. The flow of fuel in this embodiment is controlled by the 2-way valve 32 positioned between the pressurized fuel reservoir 22 and the holding chamber 18.

Figure 5:
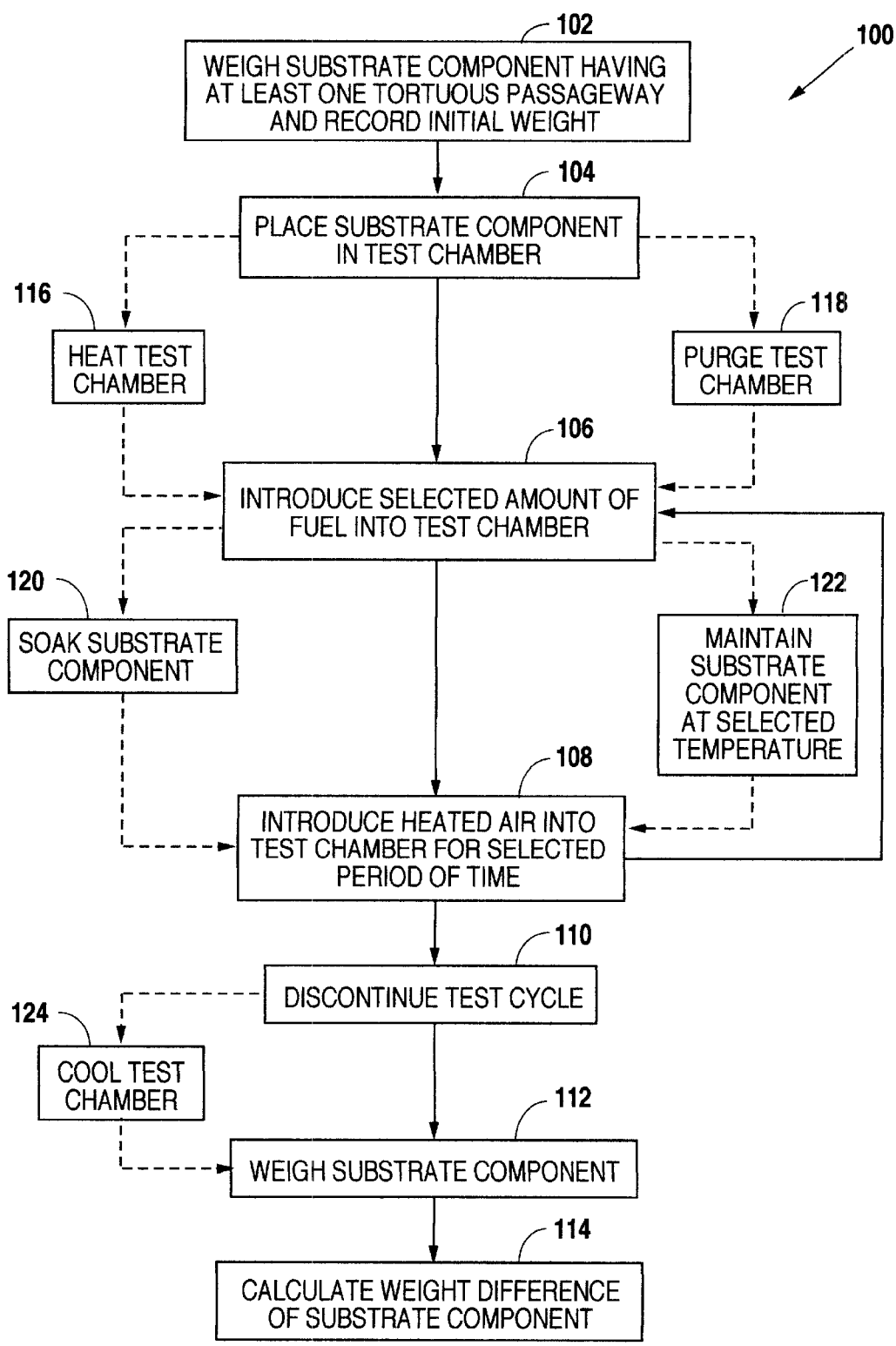
FIG. 5 is a block diagram of a method for evaluating the deposit forming characteristics of diesel fuels, diesel fuel additive substances, and mixtures of diesel fuel and additive substances in accordance with the present invention.

Under severe operating conditions, certain fuel compositions have demonstrated a propensity to form deposits around the fuel injector tip, which results in degraded performance. For example, in mountainous areas, engines experience periods of high power output, followed by operation under closed throttle conditions during which little fuel passes through the injector. However, even though fuel flow is minimal during closed throttle operation, hot air is forced into the injector during the compression stroke, causing any residual fuel to form deposits. A full-scale test procedure has been developed to simulate conditions produced during vehicle operation in a mountainous area. This test, carried out on a heavy duty Cummins L10 diesel engine, is widely recognized in the diesel engine industry and requires a controlled 125 hour test with the engine coupled to a motoring dynamometer. Under many circumstances, the cost of performing the controlled 125 hour test is prohibitive and may not definitively predict the deposit forming characteristics of a fuel when used in real world conditions, such as in vehicular applications. A method embodying the present invention for evaluating the deposit forming characteristics of diesel fuel is generally indicated in FIG. 5 by the reference numeral 100. The high temperature diesel fuel deposit test apparatus 10 embodying the present invention, has been developed to provide a cost-effective methodology to predict the deposit-forming tendencies of fuels, or the efficiency of deposit control additives. The apparatus 10 embodying the present invention, and described above, is also designed to simulate periodic rinsing of substrate surfaces with a test fuel followed by baking the substrate component in a preheated air atmosphere, thereby removing any residual fuel. That cycle closely replicates the conditions of the above-described L10 engine test. As described above, fuel and heated air, and desirably an inert gas, are introduced into the holding chamber 18 and passed through the tortuous passageways 14 that advantageously provide ample surface area for formation of fuel deposits. Following each fuel application to the substrate surface, hot air is blown through the tortuous passageways 14 to remove evaporated lighter fuel fractions and provide oxygen for deposit formation.

The testing method 100 includes initially weighing the substrate component, which in the present invention has at least one tortuous passageway 14, and the initial measured weight recorded, as represented by block 102 in FIG. 5. The substrate component is then placed in the test chamber 18, in thermal communication with the test chamber and the above-described associated heating and temperature sensing devices, as represented by block 104 in FIG. 5. In an illustrative example, the initial weight of the substrate was 78.3456 g. Desirably, after the substrate component is placed in the test chamber 18, the test chamber is sealed and heated to a selected temperature, thereby preheating the substrate component enclosed within the chamber to a selected temperature, as indicated at block 116. In the illustrative example, the test chamber 18 was heated to 165° C. (329° F.) and maintained at that temperature throughout the test. Also, it is desirable, after the substrate component has been placed in the holding chamber 18 and the chamber sealed, that the holding chamber be purged with inert gas, as indicated at block 118. Preferably this step includes maintaining a continuous flow of inert gas through the holding chamber 18 throughout the test to reduce the risk of fuel combustion or explosion.

The testing cycle, as represented by blocks 106 and 108, is then initiated. The testing cycle includes introducing selected quantities of the fuel composition under test into the test chamber 18 and distributing the fuel over the surface of the substrate component, as indicated at block 106. The fuel introduction step is carried out by actuating, with reference to FIG. 1, the fuel injector 34, or in the alternate embodiment by actuating the 2-way valve 32 for a selected period of time. By way of example, the control apparatus used In carrying out the present invention was capable of varying the fuel injection time from about 0.062 seconds to 60 seconds. In the illustrative example, fuel was injected at a pressure of 172 kPa (25 psi) for 8 ms.

Desirably, the fuel introduction step is followed by a soaking period, as indicated at block 120 and the substrate component maintained at a selected temperature during the test cycle, as indicated at block 122. At this point in the testing cycle, the test chamber is advantageously allowed to sit in a static condition for a selected period of time during which the soaking and temperature maintenance steps 120 and 122 are carried out. In the illustrative example, the soak time between fuel injections was 15 seconds.

After the introduction of the fuel composition under test into the test chamber 18, preheated air is passed through the test chamber for a selected period of time as indicated at block 108. The control apparatus used in carrying out the method described herein was capable of providing a controllable time range for introducing heated air through the test chamber 18 that ranged from 0.62 seconds to 20 hours. In the illustrative example, heated air was passed through the test chamber for 20 hours.

At the end of the heated air introduction step, as indicated at block 108, the flow of preheated air through the testing chamber 18 is discontinued, and the cycle returned to the introduction of a selected amount of fuel into the test chamber as indicated at block 106. The above steps are sequentially repeated for a selected time and number of repetitions, as desired. In the illustrative example the cycles were repeated for a period of 20 hours, during which time a total of 4.5 l of fuel was injected into the test chamber.

When the selected testing time period or selected number of test cycles has elapsed, at the completion of the final heated air introduction step 108 the testing cycle loop is exited as indicated at block 110. Desirably, a purging/cool-down step, as indicated at block 124, is carried out by purging the test chamber with inert gas and powering down the respective substrate heater 56/92. This step desirably facilitates the cooling of the test chamber 18 and the substrate component housed in the test chamber. Desirably, the cool-down step is continued until the test chamber and the substrate are brought to a temperature that permits convenient handling of the substrate component. The substrate component is then removed from the test chamber and weighed, as represented by block 112, and the initial and post-test weights are calculated as indicated at block 114. The post-test weight of the substrate was 78.3639 g, indicating that 18.3 mg of deposits were formed during the test. By way of comparison, the same fuel with the addition of 300 ppm of a candidate deposit-reducing fuel additive was tested using the same above-defined parameters. The test results with the deposit-reducing fuel additive indicated that only 7.2 mg of deposits, a significant, clearly-defined difference.

Alternatively, a selected flow of a fluid simulating exhaust gas or lubricant vapors may be passed through the test chamber 18 while carrying out the method embodying the present invention. In such an alternative embodiment, the simulated exhaust gas, lubricant vapors or other substances are conveyed to the test chamber by one or more appropriate conduits, and the flow through the conduits controlled by conventional 2-way on/off valves to simulate additional operating parameters during the test.

A wide range of operating conditions may be simulated by adjusting the temperature, volume of the airstream passing through the air chamber, and the quantity of fuel employed in the fuel introduction step. In carrying out the method embodying the present invention, the test apparatus 10, described herein, is capable of heating the test chamber and the substrate component maintained therein to a temperature of about 500° C. (932° F.). Modification of the testing method and the selected parameters are easily carried out by the use of suitable programmable controllers or computers. For example, the temperature of the substrate component and the heated air passing through the test chamber may be dynamically varied during the course of the testing cycle, further tailoring the testing conditions to simulate conditions found in an operating diesel engine.

Advantageously, the apparatus 10 and the method 100 embodying the present invention may be completely controlled by a programmable controller or computer, as well known in the art, and the test terminated if conditions exceed the selected parameters. For example, if an over-temperature or fire condition is sensed, the test can be immediately shut down and the test apparatus flooded with a blanket of $CO_2$. Moreover, test parameters may be adjusted by a computer to produce a predefined cyclic test schedule. Also, the apparatus 10 desirably provides for the test chamber to be covered by an inert gas blanket, e.g., nitrogen, to minimize fire risk during conduction of the test method embodying the present invention.

Industrial Applicability

The present invention is particularly useful in making quantitative deposit-forming or removal comparisons between different fuel compositions and additives. By way of illustration, FIG. 6 is a bar graph showing the measured fuel deposits of two fuels, fuel A and fuel B, in an engine test and in a test embodying the present invention.

Figure 6:
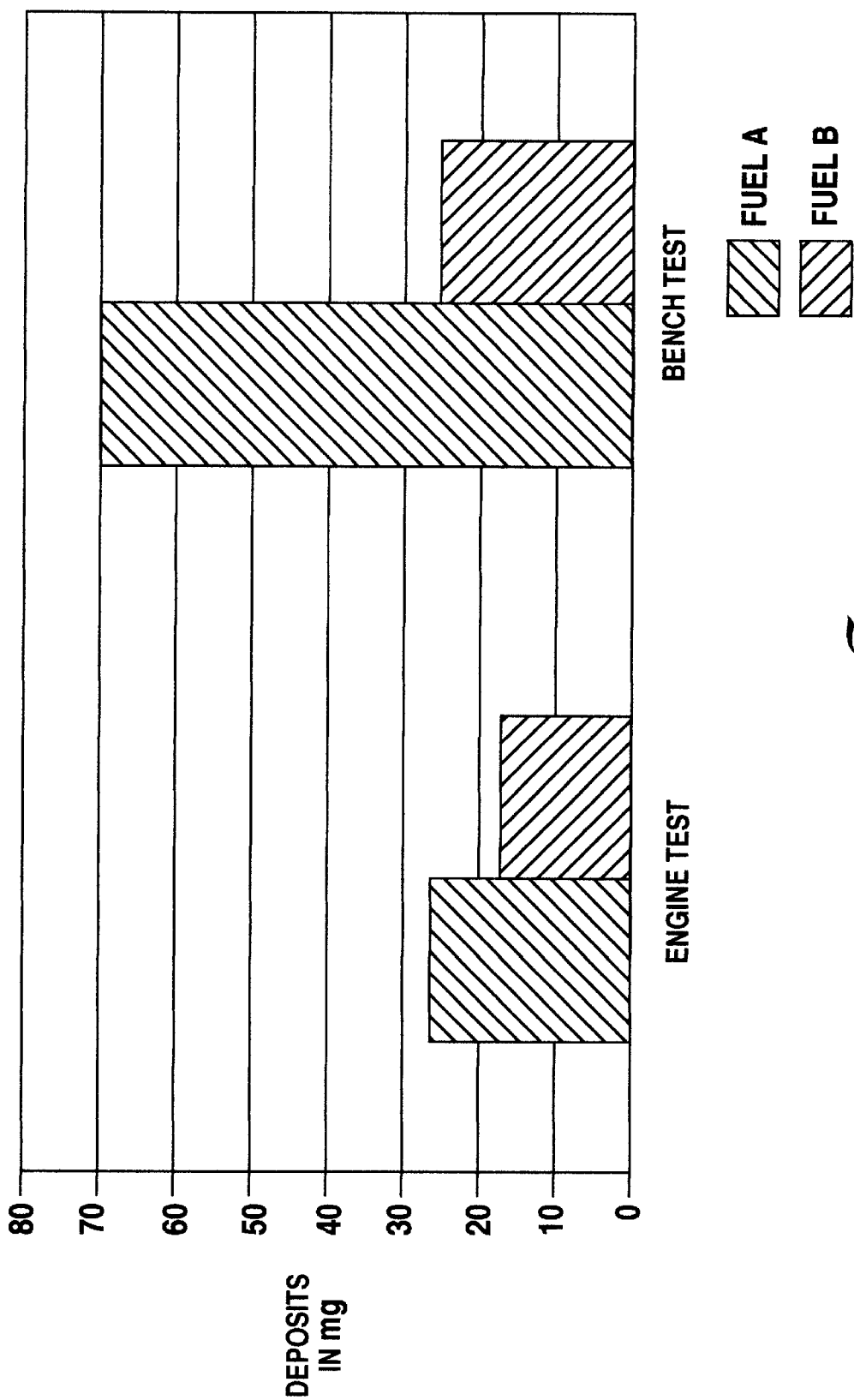
FIG. 6 is a bar graph illustrating the better-defined difference between the deposit forming characteristics of two fuels obtained by the method embodying the present invention when compared with the results obtained in an industry-accepted engine test.

The left set of bar graphs in FIG. 6 show the results obtained in a Cummins heavy duty L10 engine test, the only diesel detergent test that has met with any degree of acceptance in the U.S. The L10 engine test cycle is carried out over a 125 hour period, after which the six fuel injectors of the engine are removed and evaluated for deposits. The test results reflected in the left set of bar graphs represent the results of a 125 hour L10 test in which alternating cycles of 15 seconds full power were followed by 15 seconds of high speed motoring during which time the engine was driven by a dynamometer. That cycle replicates the conditions experienced during engine operation in mountainous areas. The test was conducted in an engine test cell with an extensive array of support systems, such as an air intake system, an exhaust system, fuel supply system, along with other control and test support systems connected to the engine after installation of the engine in the cell. After a first test of fuel A, all of the control and support systems were disconnected, the engine was uncoupled from the dynamometer and removed from the test cell. The engine was then disassembled and the engine components subjected to fuel deposit test formations were weighed and compared with an initial recorded weight of those components. The above 125 hour test procedure was then repeated with a second fuel, fuel B. The respective measured deposits formed during each of the 126 hour tests, for fuels and B, are shown side by side in the left set of bar graphs displayed in FIG. 6. As noted above, the L10 engine test is costly to carry out and time consuming. Note that the difference in measured deposits resulting from the 125 hour tests of fuel A and fuel B is only about 9 mg, with fuel B being marginally lower. That difference is of such a small magnitude that it could easily fall within the range of reasonable test error, particularly in view of the many variables involved in the L10 engine test protocol. Thus, even after conducting costly 125 hour extended engine tests, the resultant data may not be definitive of the actual deposit characteristics of the compared fuels.

Turning now to the right-hand set of bar graphs, indicating the measured deposits obtained from bench tests of the same two fuels, fuel A and fuel B, carried out in accordance with the apparatus and method of the present invention. The difference in measured deposits between fuel A and fuel B is on the order of 45 mg. This is a marked difference, clearly and unambiguously demonstrating that fuel B forms less deposits than fuel A. Thus, the bench test embodying the apparatus and method of the present invention significantly distinguishes deposit forming tendencies between fuels and fuel additives that may not be readily discernable in the previously used engine test protocols.

Although the present invention is described in terms of preferred and alternate exemplary embodiments, with specific illustrated test configuration and support equipment, those skilled in the art will recognize that changes in the specifically described embodiments may be made without departing from the spirit of the invention. For example, the configuration of the substrate component may be altered to define tortuous passageways other than those specifically described herein. Also, the illustrative test parameters and control ranges may be changed, or other steps added to the described method to further optimize the deposit-forming characteristics of specific fuels and fuel mixtures. Such changes are intended to fall within the scope of the following claims. Other aspects, features, and advantages of the present invention may be obtained from a study of this disclosure and the drawings, along with the appended claims.

What is claimed is:

1. A high temperature diesel fuel test apparatus comprising:

a substrate component having a surface defined by at least a portion of at least one tortuous passageway;

a holding chamber having an interior surface adapted to receive said substrate component and maintain a portion of said substrate component in intimate contact with the interior surface of said holding chamber;

a source of fuel selected from the group consisting of diesel fuel, diesel fuel additive substances, and mixtures of diesel fuel and diesel fuel additive substances, said source of fuel being in fluid communication with said holding chamber; and, a source of heated air in fluid communication with said holding chamber;

wherein said substrate component comprises a hollow cylinder having an outer surface at least partially defined by portions of at least one curvilinear passageway and said interior surface of the holding chamber when said hollow cylinder is disposed in said holding chamber;

wherein said apparatus includes a means for heating said substrate component, said means being disposed in the smooth bore of said hollow cylindrical member.

2. The apparatus, as set forth in claim 1, wherein said holding chamber is formed of a metallic material and said source of fuel is conveyed by a metallic conduit attached to a metallic flange of said holding chamber in biased metal-to-metal contact sufficient to provide a sole means by which an airtight seal is provided between said metallic conduit and said metallic flange of the holding chamber.

3. The apparatus, as set forth in claim 1, wherein said apparatus includes a source of an additive substance suitable for inclusion in a diesel fuel mixture, said source of additive substance being conveyed by a metal conduit in metal-to-metal contact with a metallic flange of said holding chamber thereby providing a sole means by which airtight seals are formed between said metallic conduit and said metallic flange.

4. The apparatus, as set forth in claim 1, wherein said apparatus includes a means for providing a continuous flow of an inert gas to said holding chamber.

5. The apparatus, as set forth in claim 1, wherein said apparatus includes a means for heating said substrate component.

6. The apparatus, as set forth in claim 1, wherein said holding chamber comprises a first portion and a second portion, said first portion being defined by a hollow cylinder adapted to receive said substrate component therein, and said second portion being defined by a mounting flange disposed in contiguous relationship with the first portion of said hollow cylinder.

7. The apparatus, as set forth in claim 6, wherein said hollow cylinder and said mounting flange of the holding chamber are formed of metallic materials and said mounting flange comprises a first plate and a second plate, said first plate being fixedly joined to the hollow cylinder in metal-to-metal relationship by which an airtight seal is formed between said first plate of the mounting flange and said hollow cylinder, and a second plate removably attached to said first plate in biased metal-to-metal contact sufficient to provide a sole means by which an airtight seal is formed between said first and second plates of the mounting flange.

8. The apparatus, as set forth in claim 7, wherein said source of heated air is conveyed by at least one metallic conduit attached to said mounting flange in biased metal-to-metal contact sufficient to provide a sole means by which an airtight seal is formed between said at least one metallic conduit and said mounting flange.

9. The apparatus, as set forth in claim 1, wherein said substrate component comprises a plurality of abuttingly disposed spheres each having a predefined exterior surface, and said at least one tortuous passageway being defined by the exterior surfaces of said abuttingly disposed spheres.

10. The apparatus, as set forth in claim 9, wherein said apparatus includes a means for heating said substrate component, and said holding chamber has an exterior surface, said means for heating the substrate component being disposed adjacent to the exterior surface of said holding chamber and at least a portion of said abuttingly disposed spheres being disposed in intimate contact with said interior surface of said holding chamber.

11. A method for evaluating the deposit forming characteristics of a fuel selected from the group consisting of diesel fuel, diesel fuel additive substances, and mixtures of diesel fuel and diesel fuel additive substances, comprising:
    weighing a substrate component having a surface at least partially defined by at least one tortuous passageway, and determining an initial weight of said substrate component;
    placing said weighed substrate component in a holding chamber adapted to maintain at least a portion of said substrate component in intimate contact with an interior surface of said holding chamber;
    carrying out a test cycle comprising:
        introducing a selected quantity of fuel comprising at least one of a diesel fuel, a diesel fuel additive substance, and a mixture of diesel fuel and an additive substance, into said holding chamber and onto the defined surface of the substrate component;
        passing a stream of air heated to a selected temperature through said holding chamber and over said substrate component for a selected period of time;
        repeating the steps of introducing a selected quantity of fuel onto the defined surface of the substrate component and passing a stream of air heated to a selected temperature through the holding chamber and over the surface of the substrate component, said repetition occurring continually for a selected period of time;
    discontinuing the steps of the test cycle;
    weighing the substrate component and determining the weight of the substrate component after discontinuing the test cycle; and
    calculating the difference between the initial weight of the substrate component and the weight of the substrate component after the test cycle.

12. The method, as set forth in claim 11, wherein the method includes initially heating the substrate component in the holding chamber to a selected temperature prior to beginning the test cycle.

13. A method for evaluating the deposit forming characteristics of a fuel selected from the group consisting of diesel fuel, diesel fuel additive substances, and mixtures of diesel fuel and diesel fuel additive substances, comprising:
    weighing a substrate component having a surface at least partially defined by at least one tortuous passageway, and determining an initial weight of said substrate component;
    placing said weighed substrate component in a holding chamber adapted to maintain at least a portion of said substrate component in intimate contact with an interior surface of said holding chamber;
    carrying out a test cycle comprising:
        introducing a selected quantity of fuel comprising at least one of a diesel fuel, a diesel fuel additive substance, and a mixture of diesel fuel and an additive substance, into said holding chamber and onto the defined surface of the substrate component;
        passing a stream of air heated to a selected temperature through said holding chamber and over said substrate component for a selected period of time;
        repeating the steps of introducing a selected quantity of fuel onto the defined surface of the substrate component and passing a stream of air heated to a selected temperature through the holding chamber and over the surface of the substrate component, said repetition occurring continually for a selected period of time;
    discontinuing the steps of the test cycle;
    weighing the substrate component and determining the weight of the substrate component after discontinuing the test cycle; and
    calculating the difference between the initial weight of the substrate component and the weight of the substrate component after the test cycle;
    wherein the method includes purging the test chamber with an inert gas prior to beginning a first test cycle.

14. The method, as set forth in claim 13, wherein the method includes maintaining a continuous flow of inert gas through the holding chamber throughout continuing repetitions of the test cycle.

15. The method, as set forth in claim 13, wherein the test cycle includes maintaining the substrate component at a selected temperature throughout each repetition of the test cycle.

16. The method, as set forth in claim 13, wherein the method includes maintaining the substrate component at a selected temperature for a selected period of time subsequent to introducing a selected quantity of fuel onto the surface of the substrate component during each repetition of the test cycle.

17. The method, as set forth in claim 13, wherein the method includes cooling the test chamber and the substrate component subsequent to discontinuing the test cycle and prior to weighing the substrate component after the test cycle.

18. The method, as set forth in claim 13, wherein weighing a substrate component having a surface at least partially defined by at least one tortuous passageway and determining an initial weight of the substrate component includes weighing a substrate component defined by a plurality of spheres.

19. The method, as set forth in claim 13, wherein weighing a substrate component having a surface at least partially defined by least one tortuous passageway and determining an initial weight of the substrate component includes weighing a substrate component comprising a hollow cylindrical member having an outer surface at least partially defined by a portion of a curvilinear passageway.

* * * * *